(12) United States Patent
Ziemek et al.

(10) Patent No.: US 11,376,135 B2
(45) Date of Patent: Jul. 5, 2022

(54) INSERTION INSTRUMENT WITH ARTICULATING WRIST

(71) Applicant: Zimmer Biomet Spine, Inc., Westminster, CO (US)

(72) Inventors: Terry Ziemek, Broomfield, CO (US); Patrick Hunt, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 236 days.

(21) Appl. No.: 16/359,510

(22) Filed: Mar. 20, 2019

(65) Prior Publication Data
US 2019/0216614 A1 Jul. 18, 2019

Related U.S. Application Data

(63) Continuation of application No. 14/676,046, filed on Apr. 1, 2015, now Pat. No. 10,265,194.

(51) Int. Cl.
*A61F 2/46* (2006.01)
*A61F 2/44* (2006.01)
*A61B 17/16* (2006.01)
*A61F 2/30* (2006.01)

(52) U.S. Cl.
CPC ............ *A61F 2/4611* (2013.01); *A61F 2/442* (2013.01); *A61B 17/1631* (2013.01); *A61B 17/1671* (2013.01); *A61F 2002/30471* (2013.01); *A61F 2002/30538* (2013.01); *A61F 2002/30635* (2013.01); *A61F 2002/4627* (2013.01);
(Continued)

(58) Field of Classification Search
CPC .................... A61F 2/4611; A61F 2/442; A61F 2002/4627; A61F 2002/4628; A61F 2002/4635; A61B 17/1671
See application file for complete search history.

(56) References Cited

U.S. PATENT DOCUMENTS 8,506,636 B2 * 8/2013 Dye ...................... A61F 2/4611
623/17.16
8,568,417 B2 * 10/2013 Petrzelka ........... A61B 17/1631
606/80
(Continued)

OTHER PUBLICATIONS

"U.S. Appl. No. 14/676,046, Advisory Action dated May 2, 2018", 3 pgs.
(Continued)

*Primary Examiner* — Kevin T Truong
*Assistant Examiner* — Tracy L Kamikawa

(57) ABSTRACT

A surgical instrument suitable for preparing an intervertebral disc space includes an outer sleeve, an instrument head, an inner shaft, a handle, a universal joint, a coupling member, and a drive mechanism. The outer sleeve includes a proximal end, a distal end and a longitudinal axis. The instrument head defines a longitudinal axis and is disposed at the distal end of the outer shaft. The inner shaft is slidably disposed within the outer sleeve and includes a proximal end, a distal end and a longitudinal axis coaxially aligned with the longitudinal axis of the outer sleeve. The drive mechanism is coupled between the outer sleeve and the inner shaft and actuates the outer sleeve axially relative to the inner shaft, thereby setting an angle of the longitudinal axis of the instrument head in relation to the longitudinal axis of the inner shaft.

16 Claims, 6 Drawing Sheets

(52) U.S. Cl.
CPC ............... *A61F 2002/4628* (2013.01); *A61F 2002/4635* (2013.01)

(56) References Cited

U.S. PATENT DOCUMENTS

| | | |
|---|---|---|
| 10,265,194 B2 | 4/2019 | Ziemek et al. |
| 2010/0256764 A1 | 10/2010 | Tsuang et al. |
| 2013/0072936 A1* | 3/2013 | To .................... A61B 17/1671 606/79 |
| 2014/0246471 A1 | 9/2014 | Jaworek et al. |
| 2016/0287409 A1 | 10/2016 | Ziemek et al. |

OTHER PUBLICATIONS

"U.S. Appl. No. 14/676,046, Final Office Action dated Feb. 13, 2018", 15 pgs.

"U.S. Appl. No. 14/676,046, Non Final Office Action dated Jun. 14, 2018", 12 pgs.

"U.S. Appl. No. 14/676,046, Non-Final Action with Restriction Requirement dated Sep. 20, 2017", 16 pgs.

"U.S. Appl. No. 14/676,046, Notice of Allowance dated Dec. 5, 2018", 10 pgs.

"U.S. Appl. No. 14/676,046, Response filed Apr. 12, 2018 to Final Office Action dated Feb. 13, 2018", 11 pgs.

"U.S. Appl. No. 14/676,046, Response filed Sep. 13, 2018 to Non Final Office Action dated Jun. 14, 2018", 11 pgs.

"U.S. Appl. No. 14/676,046, Response filed Dec. 20, 2017 to Non Final Office Action with Restriction Requirement dated Sep. 20, 2017", 10 pgs.

\* cited by examiner

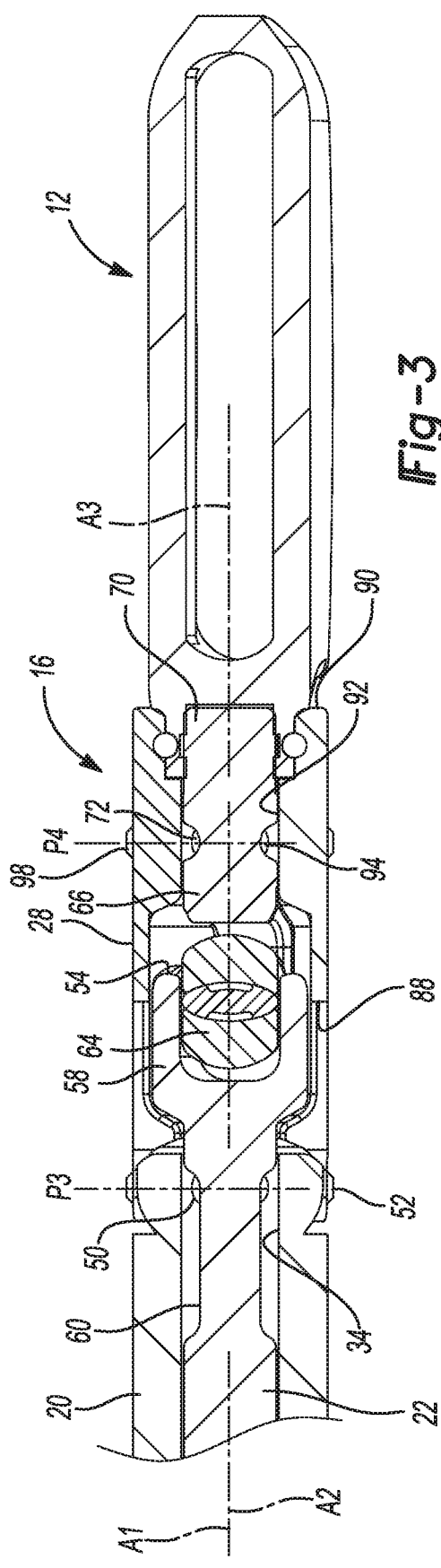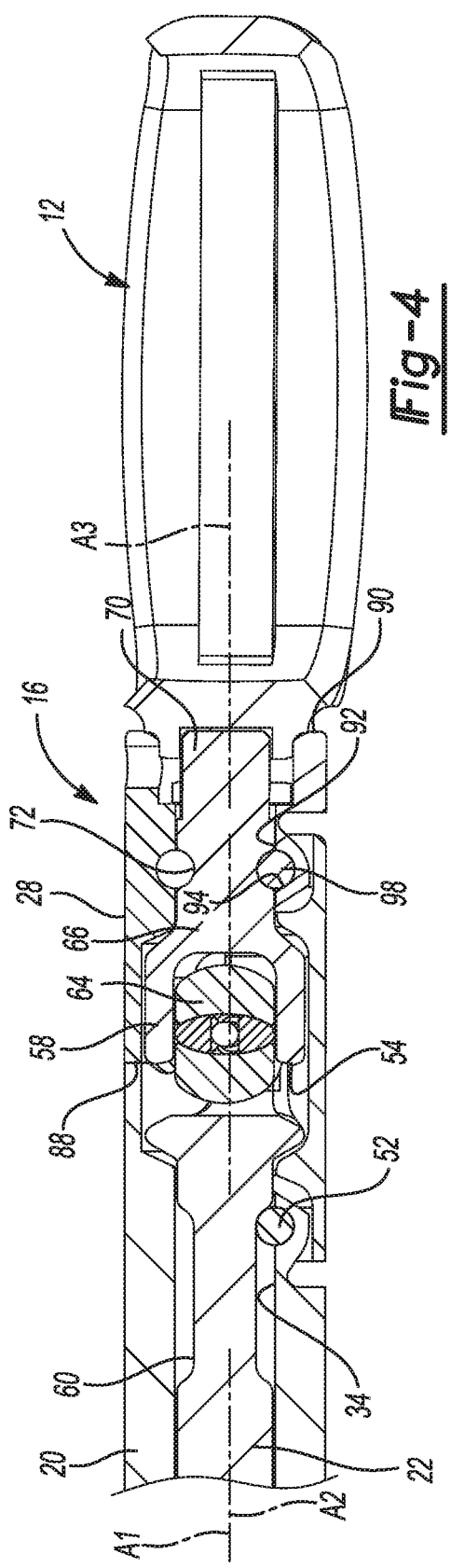

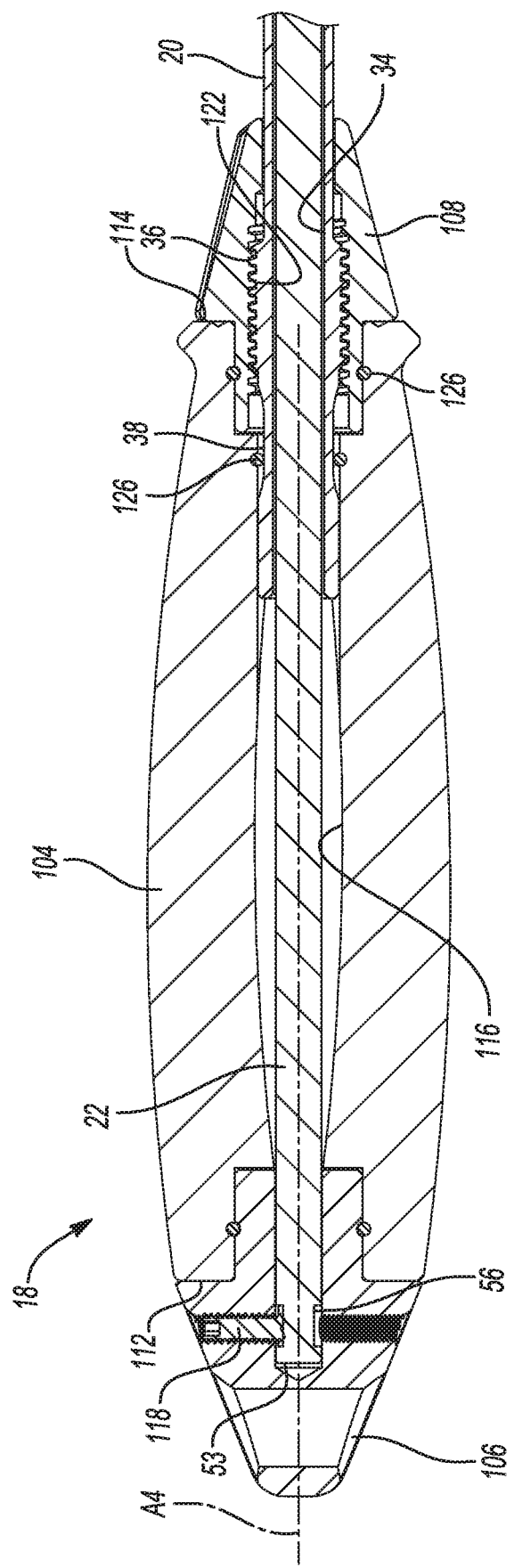

INSERTION INSTRUMENT WITH ARTICULATING WRIST

CROSS REFERENCE TO RELATED APPLICATION

The present application is a continuation of U.S. patent application Ser. No. 14/676,046, filed Apr. 1, 2015 entitled "INSERTION INSTRUMENT WITH ARTICULATING WRIST", now U.S. Pat. No. 10,265,194, which is incorporated herein by this reference in its entirety.

FIELD

The present disclosure relates to a surgical instrument, and more particularly to a surgical insertion instrument having an articulating wrist.

BACKGROUND

This section provides background information related to the present disclosure and is not necessarily prior art.

Instruments and tools are used during surgical procedures for various purposes, including providing access to a surgical site, inserting or providing materials to the surgical site, and attaching or otherwise assembling certain components at the surgical site. In some situations, it may be necessary or desirable to insert the surgical instrument into small or constrained space, or enter the surgical site from a predetermined direction, or access a predetermined location in the surgical site, or provide a portion of the surgical instrument with various manners of movement (e.g., translation, rotation, angulation, etc.) at the surgical site. For example, during some surgical procedures it may be desirable to access or otherwise approach the surgical site from a lateral direction in order to avoid a portion of the anatomy or to enter another portion of the anatomy.

While known surgical instruments have proven to be acceptable for their intended purposes, a continuous need for improvement in the relevant art remains. In this regard, it would be desirable to provide a surgical instrument that allows, or otherwise makes it easier, for a surgeon to access the surgical site and/or use and manipulate the surgical instrument at the surgical site.

SUMMARY

This section provides a general summary of the disclosure, and is not a comprehensive disclosure of its full scope or all of its features.

According to one aspect of the present disclosure, a surgical instrument suitable for preparing an intervertebral disc space is provided. The surgical instrument includes an outer sleeve, an instrument head, an inner shaft, a handle, a universal joint, a coupling member, and a drive mechanism. The outer sleeve includes a proximal end, a distal end and a longitudinal axis. The instrument head defines a longitudinal axis and is disposed at the distal end of the outer shaft. The inner shaft is slidably disposed within the outer sleeve and includes a proximal end, a distal end and a longitudinal axis coaxially aligned with the longitudinal axis of the outer sleeve. The handle is coupled to the proximal end of the inner shaft. The universal joint includes one end coupled to the distal end of the inner shaft and another end coupled to the instrument head. The coupling member includes one end pivotally coupled between the distal end of the outer sleeve and another end pivotably coupled to a retainer. The drive mechanism is coupled between the outer sleeve and the inner shaft and actuates the outer sleeve axially relative to the inner shaft, thereby setting an angle of the longitudinal axis of the instrument head in relation to the longitudinal axis of the inner shaft.

In some configurations, the instrument head includes one of a hexagonal head, a screw driver, and a drill bit.

In some configurations, the universal joint includes an annular groove and the retainer includes an aperture. The surgical instrument further includes a hinge member disposed within the aperture and the annular groove.

In some configurations, the drive mechanism includes a first drive mechanism coupled to the inner shaft and a second drive mechanism coupled to the outer shaft.

In some configurations, the surgical instrument includes a handle member.

In some configurations, the first drive mechanism is rotatable in relation to the handle member and the second drive mechanism, and the second drive mechanism is rotatable in relation to the handle member and the first drive mechanism.

In some configurations, the outer sleeve includes a first threaded portion and the second drive mechanism includes a second threaded portion threadingly engaged with the first threaded portion.

In some configurations, the outer sleeve includes a retaining feature extending from a proximal end to a distal end along the longitudinal axis.

In some configurations, a portion of the handle assembly slidably engages the retaining feature.

According to another aspect of the present disclosure, a surgical instrument is provided. The surgical instrument includes an outer sleeve, an inner shaft, a universal joint, a retainer, and a coupler. The outer sleeve includes a proximal end, a distal end, and a longitudinal axis extending between the proximal and distal ends. The inner shaft is rotatably and translatably disposed within the outer sleeve. The universal joint is pivotally coupled to the inner shaft. The retainer is configured to rotatably support the universal joint. The coupler includes a proximal end pivotally coupled to the outer sleeve and a distal end pivotally coupled to the retainer.

According to yet another aspect of the present disclosure, a method of operating a surgical instrument is provided. The surgical instrument includes an outer sleeve extending along a first axis, an inner shaft supported by the outer sleeve for rotation about the first axis, and a drive member extending along a second axis. The method includes rotating the inner shaft about the first axis to rotate the drive member about the second axis. The method also includes translating the outer sleeve along the first axis to angulate the second axis relative to the first axis.

In some configurations, the surgical instrument includes an activation member threadably engaged to the outer sleeve.

In some configurations, translating the outer sleeve along the first axis includes threading the activation member relative to the outer sleeve.

In some configurations, the surgical instrument includes an implant coupled to at least one of the inner shaft and the outer sleeve, and the method includes inserting the surgical instrument through an incision in an anterior posterior direction. The method can also include inserting the implant into an intervertebral disc space in a medial lateral direction.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a cross-sectional view of a portion of the insertion instrument with an articulating wrist of FIG. 1 taken along the line 3-3;

FIG. 4 is a cross-sectional view of a portion of the insertion instrument with an articulating wrist of FIG. 1 taken along the line 4-4

FIG. 6 is a cross-sectional view of a portion of the insertion instrument with an articulating wrist of FIG. 1 taken along the line 3-3.

Corresponding reference numerals indicate corresponding parts throughout the several views of the drawings.

DETAILED DESCRIPTION

Figure 1:
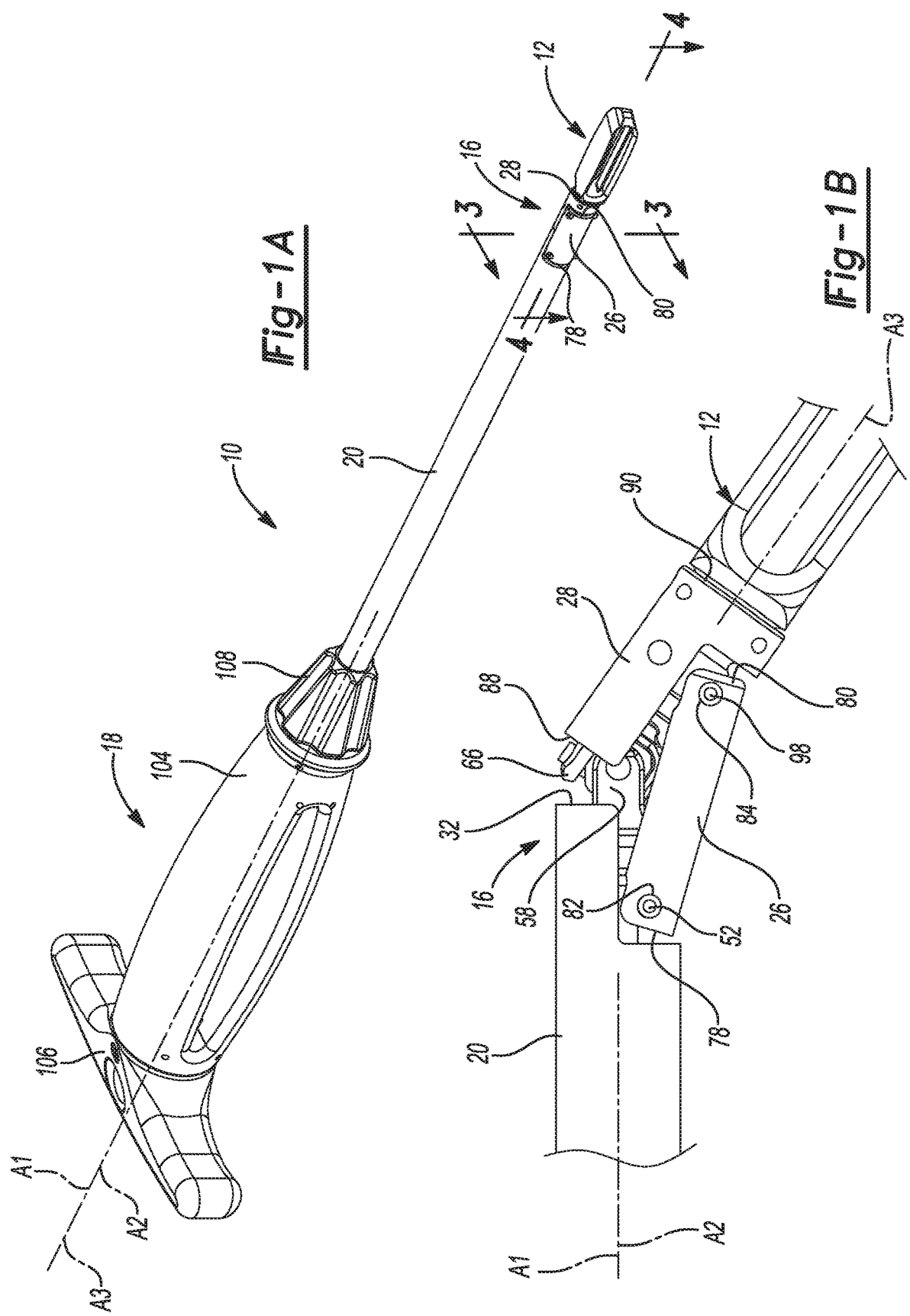
FIG. 1A is a perspective view of an insertion instrument with an articulating wrist in a first position in accordance with the principles of the present disclosure.
FIG. 1B is a perspective view of the insertion instrument with an articulating wrist of FIG. 1, the insertion instrument shown in a second position.

Example embodiments will now be described more fully with reference to the accompanying drawings.

Referring to FIG. 1A, an insertion instrument 10 with an articulating wrist constructed in accordance with the principles of the present teachings is illustrated. According to one exemplary use, the insertion instrument 10 may be used to insert an implant during a surgical procedure. Specifically, in some configurations, the insertion instrument 10 may be used to insert a spinal implant 12 into a portion of a spine 14 (FIGS. 7A and 7B), including into an intervertebral space 15 between adjacent vertebrae 17. It will be appreciated, however, that the insertion instrument 10 may have various uses within the scope of the present disclosure. For example, as will be discussed in more detail below, the insertion instrument 10 may be used for drilling or otherwise forming an aperture, driving a fastener, assembling a multi-component implant, or other similar uses.

With particular reference to FIGS. 1A, 1B and 6, the insertion instrument 10 includes an articulation assembly 16 and a handle assembly 18. As will be explained in more detail below, the articulation assembly 16 may be drivingly engaged with the handle assembly, such that manipulation (e.g., rotation) of a portion of the handle assembly 18 can cause a portion of the articulation assembly 16, and thus the implant 12, to move (e.g., rotate, translate, angulate, etc.).

Figure 2:
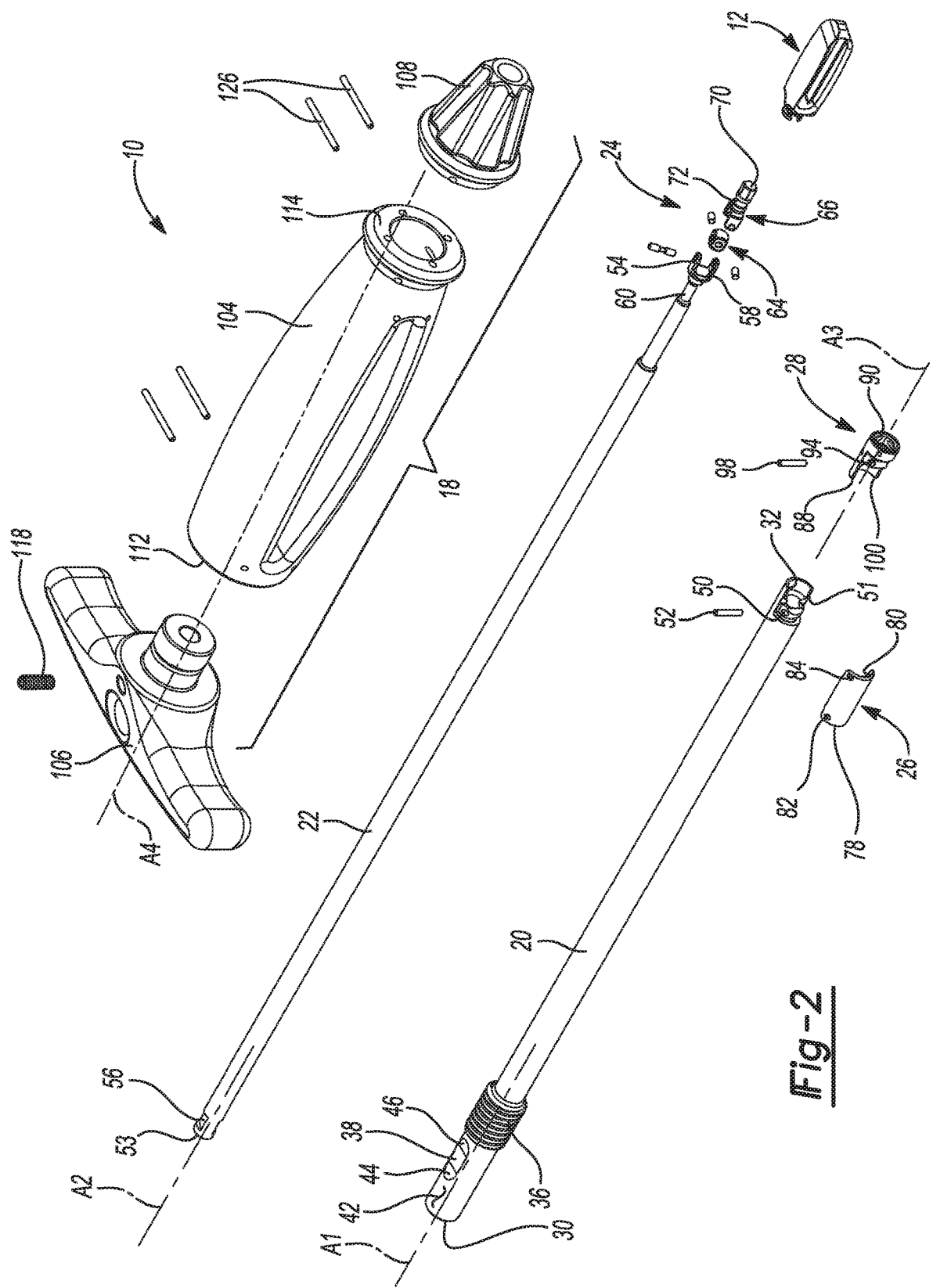
FIG. 2 is an exploded view of the insertion instrument with an articulating wrist of FIG. 1.
Figure 5:
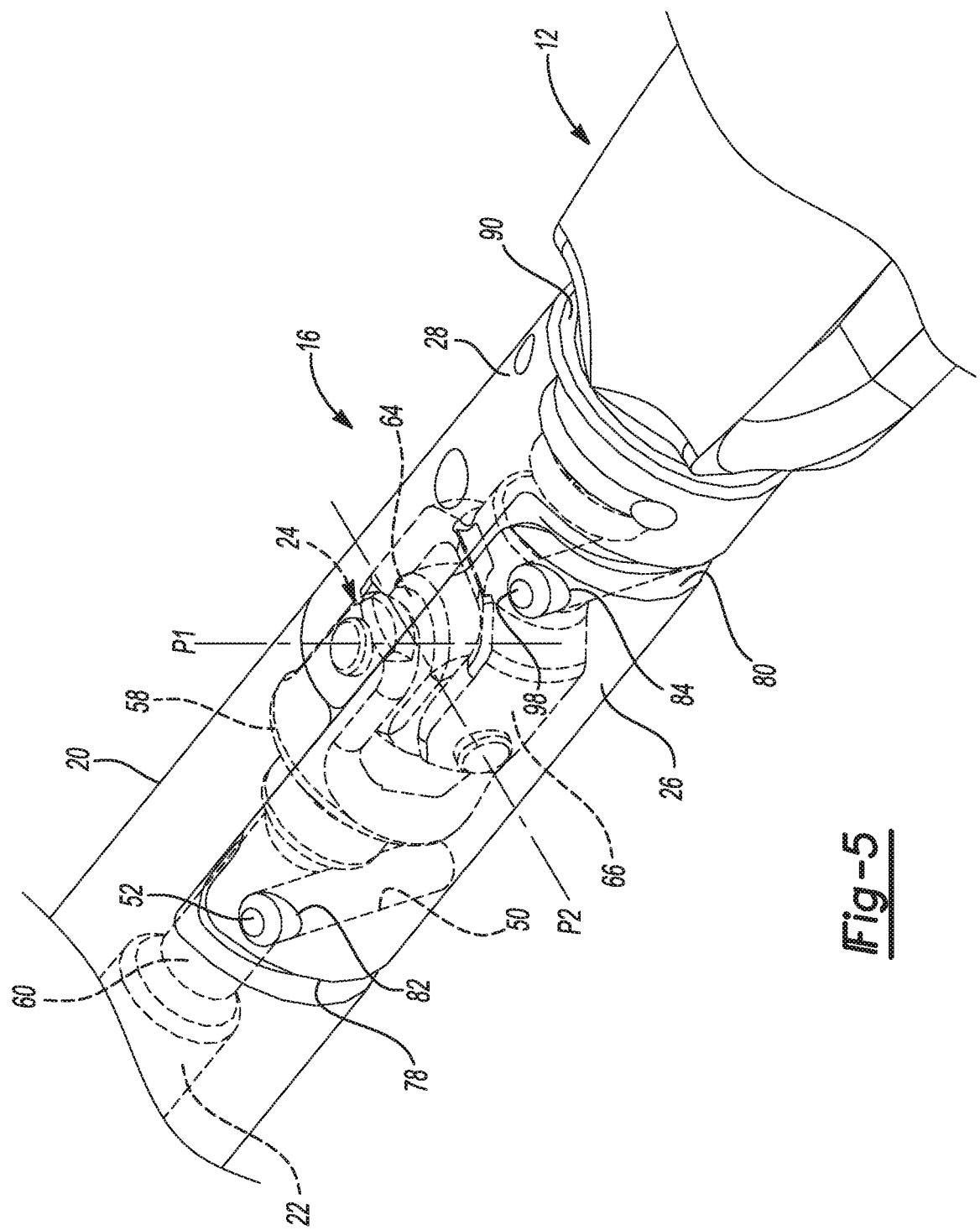
FIG. 5 is a perspective view of a portion of the insertion instrument with an articulating wrist of FIG. 1, with a portion of the insertion instrument removed for clarity.

As illustrated in FIG. 2, the articulation assembly 16 can include an outer sleeve 20, an inner sleeve or shaft 22, a universal joint 24, a coupler 26, and a retainer 28. The outer sleeve 20 includes, or otherwise extends from and between a proximal end 30 and a distal end 32 along a first longitudinal axis A1. In this regard, as illustrated in FIGS. 3 and 6, the outer sleeve 20 includes a bore 34 extending longitudinally from and between the proximal and distal ends 30, 32 of the outer sleeve 20. The proximal end 30 of the outer sleeve 20 can include a threaded portion 36 and an anti-rotation feature 38. As illustrated in FIGS. 2 and 6, the threaded portion 36 can be an outer threaded portion 36. The anti-rotation feature 38 can include a channel or groove formed in an outer surface 42 of the outer sleeve 20 between the proximal end 30 and the threaded portion 36. In this regard, the anti-rotation feature 38 can extend from a proximal end 44 to a distal end 46 along the first longitudinal axis A1. As will be explained in more detail below, the distance along the first longitudinal axis A1, between the proximal end 44 and the distal end 46 of the anti-rotation feature 38, can define a maximum travel distance of the outer sleeve 20 relative to the inner shaft 22 along the first longitudinal axis A1.

As illustrated in FIG. 2, the distal end 32 of the outer sleeve 20 can include a first pivot feature or hinge 50. The hinge 50 can be an aperture formed in the outer sleeve 20, and a pin member 52. As will be explained in more detail below, in an assembled configuration, the hinge 50 can pivotally couple the outer sleeve 20 to the coupler 26. As illustrated, the distal end 32 of the outer sleeve 20 can also include a cut-away or recessed portion 51, such that the distal end 32 of the outer sleeve 20 defines a portion of a cylinder (e.g., a semi-cylindrical construct).

With further reference to FIG. 2, the shaft 22 includes, or otherwise extends from and between a proximal end 53 and a distal end 54 along a second longitudinal axis A2. In an assembled configuration, the shaft 22 can be rotatably and translatably disposed within the bore 34 of the outer sleeve 20, such that the second longitudinal axis A2 is parallel to the first longitudinal axis A1. In this regard, the shaft 22 is configured to rotate within the outer sleeve 20 about the second longitudinal axis A2, and translate within the outer sleeve 20 along the second longitudinal axis A2.

The shaft 22 can include a first retaining feature or groove 56 disposed near the proximal end 53, a hinge mechanism or yoke 58 disposed near the distal end 54, and a retaining feature or reduced diameter portion 60 disposed between the proximal and distal ends 53, 54. As will be explained in more detail, below, in the assembled configuration the groove 56 can secure the shaft 22 to the handle assembly 18, and the hinge mechanism 58 can be pivotally coupled to the universal joint 24. In this regard, the hinge mechanism 58 can define a first pivot axis P1 of the universal joint 24. As will be explained in more detail below, the reduced diameter portion 60 can help to secure the shaft 22 within the outer sleeve 20, and/or further define the maximum travel distance of the outer sleeve 20 relative to the inner sleeve 22 along the first longitudinal axis A1. In this regard, with reference to FIGS. 3 and 4, the pin 52 can create or otherwise define a reduced diameter portion of the bore 34 of the outer sleeve 20 that is substantially equal to, or slightly greater than, an outer diameter of the reduced diameter portion 60 of the shaft 22. Accordingly, the shaft 22 is at least partially supported for rotation and translation by the pin 52.

As illustrated in FIG. 2, the universal joint 24 can include a spider or cross-piece 64 and a hinge mechanism or yoke 66. The hinge mechanism 66 can define a second pivot axis P2 of the universal joint 24. The second pivot axis P2 is perpendicular to the first pivot axis P1. In this regard, in the assembled configuration, the hinge mechanism 58 of the shaft 22 can be pivotally coupled to the cross-piece 64 for pivotal rotation about the first pivot axis P1, and the hinge mechanism 66 of the universal joint 24 can be pivotally coupled to the cross-piece 64 for pivotal rotation about the second pivot axis P2.

With reference to FIGS. 2 and 3, the hinge mechanism 66 may further include an instrument head or driving feature 70 and a retaining feature 72. The driving feature 70 and the second pivot axis P2 may be disposed at opposite ends of the hinge mechanism 66. As illustrated in FIG. 2, the driving feature 70 can include a hex head or other similar feature that can drivingly engage, or otherwise mate with, the implant 12. In this regard, it will also be appreciated that the driving feature 70 may include, or otherwise be configured to mate with, other surgical tools or implants, such as drill bits, fasteners, pins, and other similar components. The retaining feature 72 can be disposed between the second pivot axis P2 and the driving feature 70. As illustrated in at least FIG. 2, in some configurations, the retaining feature 72 can include an annular groove or channel. As will be explained in more detail below, in the assembled configuration, the retaining feature 72 can help to rotatably secure the hinge mechanism 66 within the retainer 28.

The coupler 26 can extend from a proximal end 78 to a distal end 80. In some configurations, the coupler 26 may include or otherwise define a portion of a cylinder extending from and between the proximal and distal ends 78, 80. In this regard, in the assembled configuration, the coupler 26 may mate with, or otherwise be received by, the recessed portion 51 of the outer sleeve, such that the distal end 32 of the outer sleeve 20 and the coupler 26 collectively define a substantially cylindrical construct.

The proximal end 78 of the coupler 26 includes a first pivot or hinge feature 82, and the distal end 80 includes a second pivot or hinge feature 84. As illustrated in FIG. 2, in some configurations, the first and second hinge features 82, 84 can each include a pair of aligned apertures. In the assembled configuration, the first hinge feature 82 can be pivotally coupled to the outer sleeve 20, and the second hinge feature 84 can be pivotally coupled to the retainer 28. In this regard, in the assembled configuration, the pin 52 can be rotatably received by at least one of the first hinge feature 82 and the hinge 50 of the outer sleeve 20, such that the coupler 26 is pivotally coupled to the outer sleeve 20, as described above.

The retainer 28 includes, or otherwise extends from and between a proximal end 88 and a distal end 90 along a third longitudinal axis A3. In this regard, as illustrated in FIG. 3, the retainer 28 includes a bore 92 extending longitudinally from and between the proximal and distal ends 88, 90. The bore 92 is sized and shaped to receive a portion of the hinge mechanism 66 (e.g., the driving feature 70) for rotation therein. The proximal end 88 of the retainer 28 can include a second pivot feature or hinge 94 that is substantially similar to the first pivot feature or hinge 50 formed in the outer sleeve 20. In this regard, the hinge 94 can include an aperture formed in the retainer 28, and a pin 98. As illustrated in FIG. 3, the pin 98 and the pin 52 may define parallel pivot axes P3, P4, respectively. In the assembled configuration, the pin 98 can be rotatably received by at least one of the second hinge feature 84 of the coupler 26 and the hinge 94 of the retainer 28, such that the retainer 28 is pivotally coupled to the coupler 26. In this regard, as illustrated in FIG. 3, the pin 98 can be received within the retaining feature 72 of the hinge mechanism 66, such that the pin 98 can allow the hinge mechanism 66 to rotate within the bore 92 about the third longitudinal axis A3, and can prevent the hinge mechanism 66 from translating within the bore 92 in a direction parallel to the third longitudinal axis A3. In this regard, as illustrated in FIG. 4, in the assembled configuration, the pin 98 can be slidably received within the groove 72.

As illustrated in FIG. 2, the proximal end 88 of the retainer 28 can also include a cut-away or recessed portion 100, such that the proximal end 88 of the retainer 28 defines a portion of a cylinder (e.g., a semi-cylindrical construct). In this regard, in the assembled configuration, the coupler 26 may mate with, or otherwise be received by, the recessed portion 100 of the retainer 28, such that the coupler 26 and the proximal end 88 of the retainer 28 collectively define a substantially cylindrical construct.

With reference to FIGS. 1, 2 and 6, the handle assembly 18 includes a handle 104, a first drive or actuation mechanism 106, and a second drive or actuation mechanism 108. As will be explained in more detail below, the first and second actuation mechanisms 106, 108 can be rotatably coupled to the handle 104 and configured to drive or actuate the shaft 22 and the outer sleeve 20, respectively, and cause the hinge mechanism 66 to rotate about the third longitudinal axis A3, and/or to cause the hinge mechanism 66 and third longitudinal axis A3 to angulate relative to the first longitudinal axis A1.

The handle 104 includes, or otherwise extends from and between a proximal end 112 and a distal end 114 along a fourth longitudinal axis A4. In this regard, as illustrated in FIG. 6 the handle 104 includes a bore 116 extending longitudinally from and between the proximal and distal ends 112, 114 of the handle 104. The bore 116 can be sized and shaped to rotatably receive the outer sleeve 20, the inner shaft 22, and the first and second actuation mechanisms 106, 108 at the proximal and distal ends 112, 114, respectively, of the handle 104.

As illustrated in FIG. 6, the first actuation mechanism 106 is coupled to the shaft 22 and rotatably received within the bore 116 of the handle 104. In this regard, in the assembled configuration the shaft 22 may be coupled to the first actuation mechanism 106 with a set screw 118, for example, such that rotation of the first actuation mechanism 106 causes the rotation of the shaft 22 about the second longitudinal axis A2, and in turn, rotation of the hinge mechanism 66 and the drive feature 70 about the third longitudinal axis A3.

With continued reference to FIG. 6, the second actuation mechanism 108 is coupled to the outer sleeve 20 and rotatably received within the bore 116 of the handle 104. In this regard, the second actuation mechanism 108 may include an internally threaded portion 122 configured to engage the threaded portion 36 of the outer sleeve 20. Accordingly, and as will be explained in more detail below, in the assembled configuration, rotation of the second actuation mechanism 108 relative to the handle 104 can cause the threaded portion 122 of the second actuation mechanism 108 to threadably engage the threaded portion 36 of the outer sleeve, and in turn, cause the outer sleeve 20 to translate within the bore 116 and along the first longitudinal axis A1.

With continued reference to the figures, operation of the insertion instrument 10 will now be described in more detail. In a first mode of operation, a surgeon may choose to rotate the driving feature 70, or the implant 12 coupled thereto, for example, about the third longitudinal axis A3. In this regard, in the first mode of operation, the surgeon may rotate the first actuation mechanism 106 relative to the handle 104 about the fourth longitudinal axis A4, to cause the shaft 22 and the driving feature 70, coupled thereto in the manner described above, to rotate about the second and third longitudinal axes A2, A3, respectively. Accordingly, the driving feature 70 and/or the implant 12 may rotate from a first position (FIG. 1A) to a second position (FIG. 1B) about the third longitudinal axis A3.

Figure 7A:
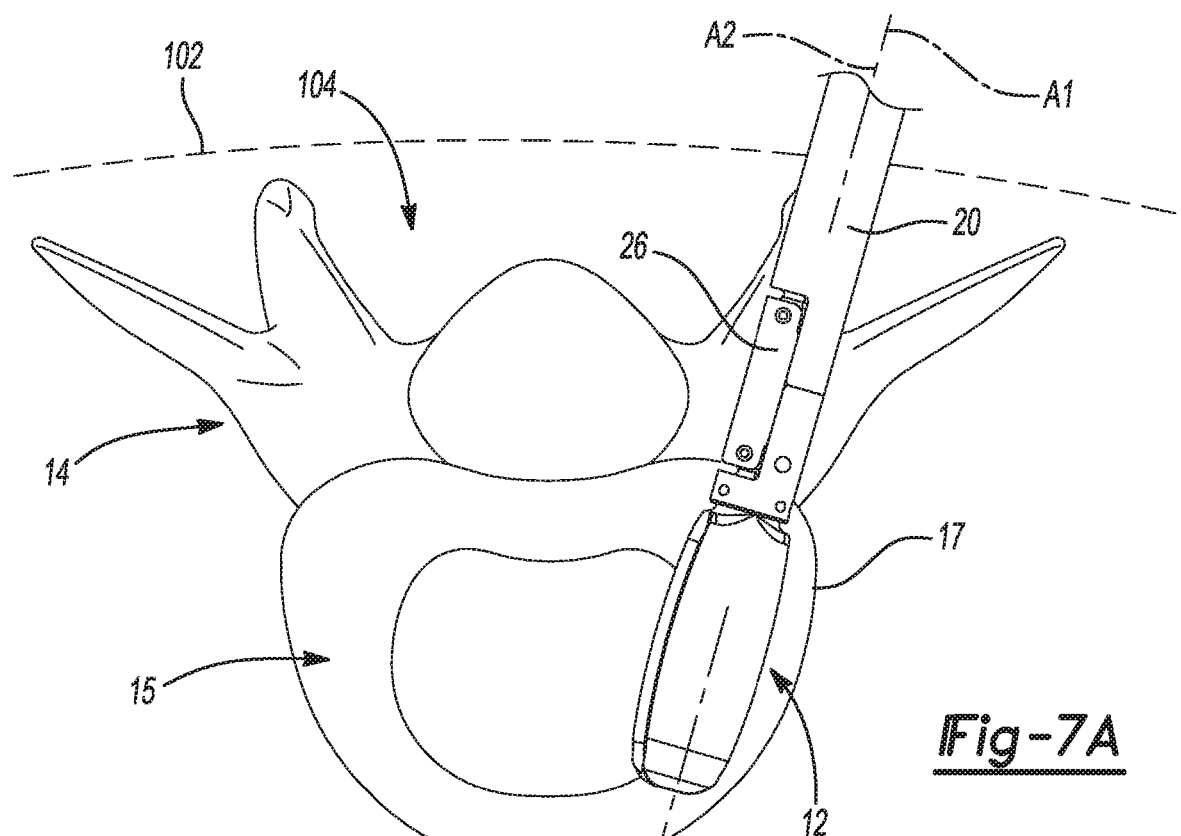
FIG. 7A is an environmental view of the insertion instrument with an articulating wrist of FIG. 1 in a first mode of operation.
Figure 7B:
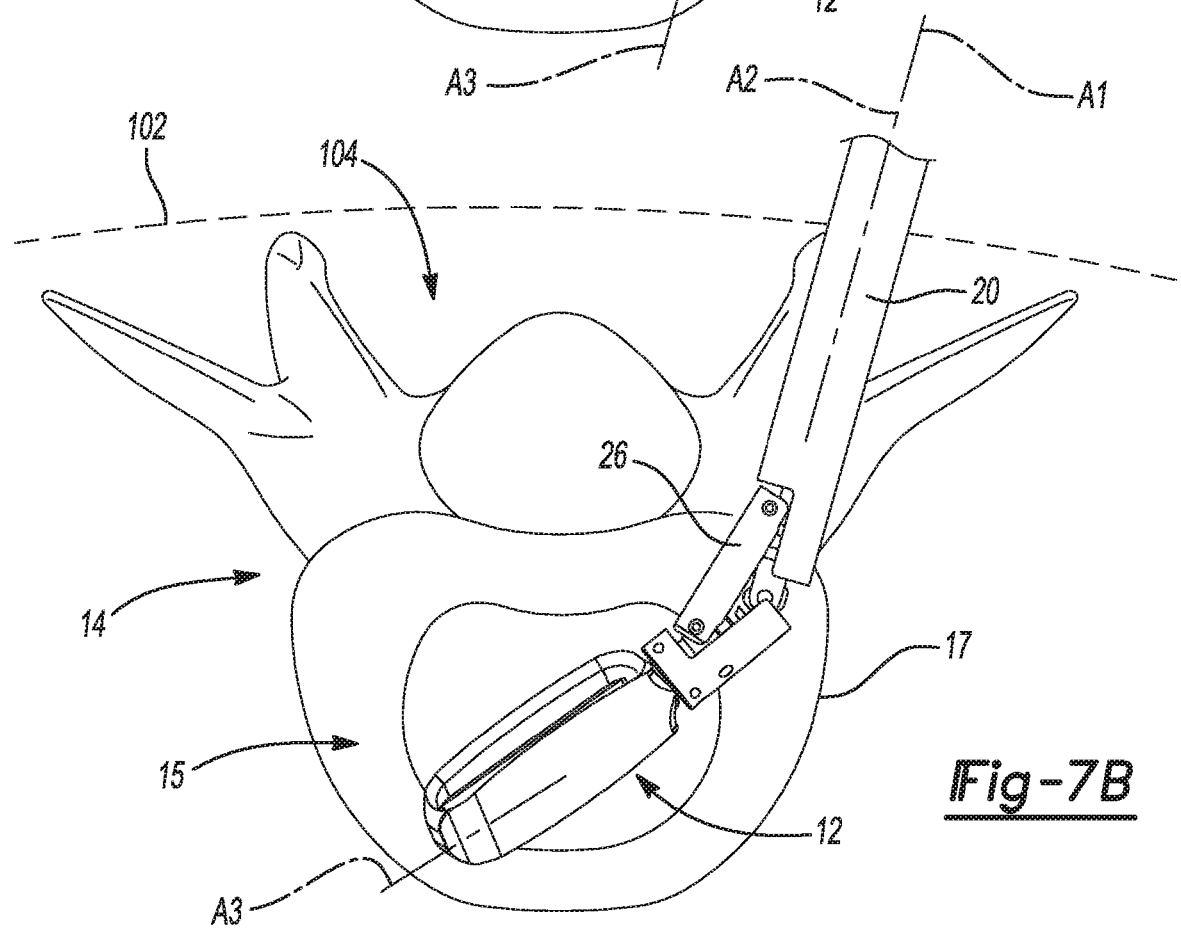
FIG. 7B is an environmental view of the insertion instrument with an articulating wrist of FIG. 1 in a second mode of operation.

With reference to FIGS. 7A and 7B, in an exemplary surgical procedure, the first mode of operation may include creating an incision 102 in a patient to provide access to a surgical site 104 from a first direction. For example, the incision 102 may be aligned with the patient's spine 14, and provide access to the patient's spine 14 from an anterior-posterior direction. Accordingly, the implant 12 may be inserted into the incision in the anterior-posterior direction while the instrument 10 is in the first position (FIG. 7A).

In a second mode of operation, the surgeon may choose to angulate the third longitudinal axis A3 or the driving feature 70 relative to the second longitudinal axis A2 of the shaft 22. The second mode of operation can occur before, after, or concurrently with the first mode of operation. Specifically, the surgeon may rotate the second actuation mechanism 108 relative to the handle 104 about the fourth longitudinal axis A4. As the surgeon rotates the second actuation mechanism 108, the threaded portion 122 of the second actuation mechanism 108 will threadably engage the threaded portion 36 of the outer sleeve 20. In this regard, the handle assembly 18 may further include at least one second anti-rotation feature or pin 126. In the assembled configuration, the pin 126 will engage the anti-rotation feature 38 formed in the outer sleeve 20 to prevent the outer sleeve from rotating relative to the handle 104. As the outer sleeve 20 threadably engages the second actuation mechanism 108, the outer sleeve will translate relative to the handle 104, and thus the shaft 22, along the first longitudinal axis A1. As the outer sleeve 20 translates along the first longitudinal axis A1, the coupler 26 will restrain the distance between the hinge 94 of the retainer 28 and the hinge 50 of the outer sleeve 20, while the pin 98 and the retaining feature 72 of the hinge mechanism 66 can prevent the retainer 28 from translating relative to the hinge mechanism 66 along the third longitudinal axis A3. Accordingly, as the outer sleeve 20 translates along the first longitudinal axis A1, the hinge mechanism 66 is forced to pivot about the first and/or second pivot axes P1, P2, thus allowing the third longitudinal axis A3 to angulate relative to the first longitudinal axis A1 from the first position (FIG. 7A) to the second position (FIG. 7B). As illustrated in FIGS. 7A and 7B, the first longitudinal axis A1 may remain in the same position in both the first and second modes of operation.

In an exemplary surgical procedure, the second mode of operation may include directing or otherwise moving the driving feature 70 and/or the implant 12 in a second direction transverse to the first direction. For example, as illustrated in FIGS. 7A and 7B, in a spinal surgery procedure, the surgeon may direct the driving feature 70 and/or the implant 12 into the surgical site 104, such as the intervertebral disc space 15 of the spine 14 for example, in a medial-lateral direction, while a portion of the instrument 10 extends through the incision 102 in the anterior-posterior direction. Accordingly, as illustrated in FIG. 7B, the implant 12 may be inserted into the intervertebral disc space 15 while the outer sleeve 20 remains in the first position (FIG. 7A).

The adjustability (e.g., rotation) of the driving feature 70 about the third longitudinal axis A3, and the adjustability of the third longitudinal axis (e.g., angulation) relative to the first longitudinal axis A1 can allow the surgeon to move the driving feature 70 and/or the implant 12 into a plurality of positions. As such, the adjustability of the driving feature 70 and/or the implant 12 can allow the surgeon to access the surgical site 104 from various directions and in various configurations to perform a variety of procedures at the surgical site 104.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A method of operating a surgical instrument including an outer sleeve extending along a first axis, an inner shaft supported by the outer sleeve rotatable about the first axis, a drive member extending along a second axis, and a coupling member pivotably connected to the outer sleeve and a retainer containing the drive member, the method comprising:
   rotating the inner shaft about the first axis to rotate the drive member about the second axis; and
   translating the outer sleeve along the first axis causing the coupling member to pivot about first and second pivot points to angulate the second axis relative to the first axis, wherein the translating the outer sleeve causes the first pivot point to translate relative to the inner shaft and concurrently causes a retaining feature in the drive member to prevent linear translation of the second pivot point relative to the drive member,
   wherein the translating the outer sleeve includes a pin forming the second pivot point interacting with the retaining feature in the form of an annular groove to prevent linear translation of the second pivot point relative to the drive member.

2. The method of claim 1, wherein the surgical instrument includes an activation member threadably engaged to the outer sleeve, and wherein the translating the outer sleeve along the first axis includes threading the activation member relative to the outer sleeve.

3. The method of claim 1, wherein the surgical instrument includes an implant coupled to at least one of the inner shaft and the outer sleeve, the method further comprising:
   inserting the surgical instrument through an incision in an anterior posterior direction; and
   articulating the implant into an intervertebral disc space in a medial lateral direction.

4. The method of claim 3, wherein the articulating the implant is caused by the translating the outer sleeve.

5. The method of claim 3, further comprising rotating a first actuation mechanism disposed on a proximal end of a handle assembly coupled to the inner shaft to release the implant within the intervertebral disc space.

6. The method of claim 5, wherein the translating the outer sleeve includes rotating a second actuation mechanism disposed on a distal end of the handle assembly.

7. The method of claim 1, wherein the translating the outer sleeve includes causing the coupling member to restrain a distance between a first hinge on the outer sleeve and a second hinge on the retainer.

8. The method of claim 1, wherein the translating the outer sleeve includes linearly shifting the outer sleeve along the first axis relative to at least a portion of the inner shaft.

9. A method comprising:
   rotating an inner shaft extending along a first axis of a surgical instrument and contained within an outer sleeve to rotate an implant attached to a drive member around a second axis, the drive member contained within a retainer and coupled to the inner shaft through a universal joint; and
   translating the outer sleeve along the first axis causing a coupling member pivotably coupled to the outer sleeve by a first pivot point and the retainer by a second pivot point to angulate the second axis relative to the first axis, wherein the translating the outer sleeve causes the first pivot point to translate relative to the inner shaft and concurrently a retaining feature on the drive member prevents linear translation of the second pivot point relative to the drive member,
   wherein the translating the outer sleeve includes a pin forming the second pivot point interacting with the retaining feature in the form of an annular groove to prevent linear translation of the second pivot point relative to the drive member.

10. The method of claim 9, wherein the surgical instrument includes an activation member threadably engaged to the outer sleeve, and wherein the translating the outer sleeve along the first axis includes threading the activation member relative to the outer sleeve.

11. The method of claim 9, further comprising:
    inserting the surgical instrument through an incision in an anterior posterior direction; and
    articulating the implant into an intervertebral disc space in a medial lateral direction.

12. The method of claim 11, wherein the articulating the implant is caused by the translating the outer sleeve.

13. The method of claim 11, further comprising rotating a first actuation mechanism disposed on a proximal end of a handle assembly coupled to the inner shaft to release the implant within the intervertebral disc space.

14. The method of claim 13, wherein the translating the outer sleeve includes rotating a second actuation mechanism disposed on a distal end of the handle assembly.

15. The method of claim 9, wherein the translating the outer sleeve includes causing the coupling member to restrain a distance between a first hinge on the outer sleeve and a second hinge on the retainer.

16. The method of claim 9, wherein the translating the outer sleeve includes linearly shifting the outer sleeve along the first axis relative to at least a portion of the inner shaft.

* * * * *